United States Patent [19]
Gayst

[11] 4,083,224
[45] Apr. 11, 1978

[54] PHASE TRANSITION DETECTOR

[75] Inventor: Stephen Gayst, Bellevue Hill, Australia

[73] Assignee: The University of Sydney, Australia

[21] Appl. No.: 727,626

[22] Filed: Sep. 28, 1976

[30] Foreign Application Priority Data

Sep. 29, 1975 Australia .............................. 3370/75

[51] Int. Cl.² .......................................... G01N 25/68
[52] U.S. Cl. .................................................. 73/17 A
[58] Field of Search .............................. 73/17 A, 17 R

[56] References Cited
U.S. PATENT DOCUMENTS

| 3,319,457 | 5/1967 | Leone | 73/17 |
| 3,416,356 | 12/1968 | Bridgeman | 73/17 |
| 3,623,356 | 11/1971 | Bisberg | 73/17 |

Primary Examiner—Herbert Goldstein

[57] ABSTRACT

A dewpoint detector has a mirror which clouds over when condensation forms on it and this is detected by attenuation of a light beam reflected from the mirror. The precise temperature of the mirror is ascertained by a thermister which is buried just beneath the mirror surface and has its leads bonded to the mirror which provides a heat sink. Cooling of the mirror is effected by Peltier cooling. The detector can be used to determine freezing points accurately, as well as dewpoints.

13 Claims, 4 Drawing Figures

PHASE TRANSITION DETECTOR

FIELD OF THE INVENTION

This invention relates to the construction of a Peltier Effect device having electrical circuitry associated with an optical system incorporating a mirror and used to sense when a transition temperature is reached at which a change in phase occurs.

The term 'transition temperature' is used in this specification to denote a temperature at which a constituent of a fluid environment of the mirror undergoes a change of state resulting in a change in attenuation of an optical path which includes the mirror. One example of a transition temperature is the dewpoint temperature at which condensation of a constituent of a gas fluid occurs on the mirror to cloud it. Another example is the freezing temperature of a liquid constituent of a liquid fluid. Thus the device of the invention is not be be considered solely as a dewpoint detector as it has applications anywhere where a very accurate measurement of a transition temperature is useful to provide information relating to the environment of the device.

STATE OF THE ART

The use of a mirror to detect the onset of dew-point is well known. A collimated beam of light is reflected from the mirror to a light sensor and clouding of the mirror caused by the formation of condensation on it, reduces its reflectivity and the diffusion of the light which results causes the light intensity incident on the light sensor to fall. An electrical output from the sensor indicates the fall and by monitoring the temperature of the atmosphere in the vicinity of the mirror one can determine the temperature at which condensation formed and thus the dewpoint temperature. Hitherto such apparatus has been unable to measure the dewpoint temperature very accurately.

OBJECT OF THE INVENTION

An object of this invention is the provision of an accurate detector for signifying a phase transition.

THE INVENTION

In accordance with the present invention a device for use in determining a phase transition temperature such as the dewpoint temperature of a vapour, comprises a member having good thermal and electrical conducting properties which is arranged to be cooled by a Peltier Effect junction and has a discrete area providing an exposed mirror surface whose reflective properties deteriorate suddenly when clouded by the occurrence of the transition temperature, the mirror surface temperature being sensed by a temperature-sensitive electrical component buried in the member and having two electrical connections clamped thermally to the member which thus provides a heat sink therefore, one of the connections being mechanically and electrically connected to the member which is provided at a remote location with a lead for completing the electrical circuit to said one connection of the component.

PREFERRED FEATURES OF THE INVENTION

The member, which may comprise high conductivity copper with a plated layer of nickel on one side providing the mirror area, serves to conduct heat away from the mirror area as well as to isolate at least one lead of the electrical component from external temperature changes.

Preferably the electrical component is provided with a second lead which is thermally clamped to the member, for example by being wound a few times around its periphery and clamped firmly to it while being electrically insulated from it. A groove may be provided in the rim of the member for this purpose. The clamped turns of the lead may comprise a wire known in the trade as 'constantine' wire which has an electrical resistance which is relatively insensitive to temperature. This constantine wire may be bonded at one end to one connection of the component preferably at a position close to the member.

The invention will now be described in more detail, by way of example, with reference to the accompanying drawings in which:

THE DRAWINGS

DESCRIPTION OF PREFERRED EMBODIMENT

Figure 1:
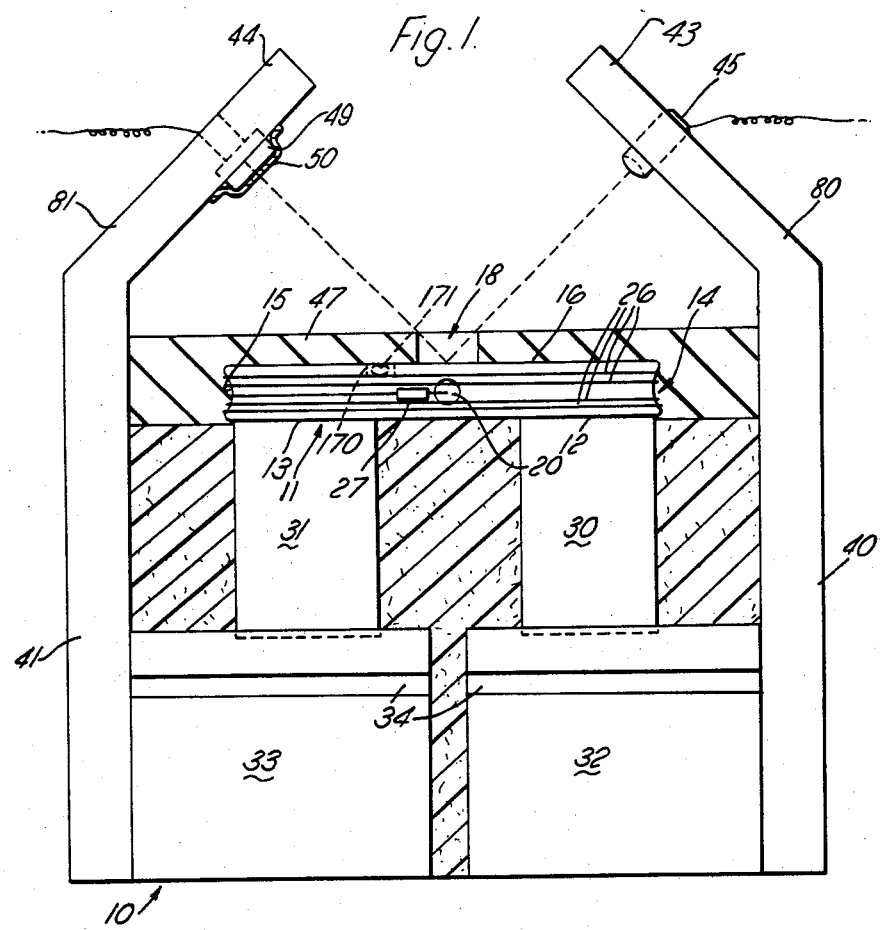
FIG. 1 is a diagrammatic side view of a dewpoint detecting device partially broken away.

The device shown in FIG. 1 referenced 10 and comprises a member 11 providing a bridge between two Peltier junctions 12 and 13. The member 11 is of composite construction and comprises a copper base 16 having a peripheral shallow groove 15 and to the top face of which is a heavily deposited layer of plated nickel which is cut back so that it is only a few hundred microns thick and highly polished to provide a good reflecting surface. A discrete area of about 1/16th of a square inch of the surface is exposed at 18. The remainder is covered by a thick layer 47 of red silicone rubber which has good thermal insulating properties and is known as SILASTIC "D" RTV made by Dow Corning Corporation of America.

The copper base 14 of the bridge 11 is provided with a lateral bore 20 midway between the junctions 12 and 13. Located within the bore but disposed on one side of the area 18 is a thermister bead 21 shown in FIG. 2, and of naked minature bead typed No. 2322-6301474 available from Philips Industries Holdings Limited of Holland. Pre-aging the bead for 2 to 6 hours at about 198° C prior to fitting it in the bore is necessary to enhance reliability. This bead has two connecting wires one of which, referenced 22, is doubled back around the side of the bead and conductively secured at 23 within the bore 20 to the copper base 14. The bead 21 is held in place by a heat conducting silicone resin putty marketed by Jeramyn of Australia and known as "Thermaflow". The other connection wire 24 is led out centrally through the bore 20 and welded at 25 to one end of a length of a constantine wire 26 which is wound several times around the member 11 so as to lie within the groove 15. A spacer tube 27 acts as a stand-off to hold the weld of the constantine wire to the connection wire 24, clear of the member 11. The constantine wire is electrically insulated throughout its length by an insulator having good thermal conducting properties. The resin used in the bore is also used to heat clamp the constantine wire 26 firmly to the peripheral rim of the member 11.

Returning to FIG. 1, the two Peltier-Effect junctions are connected in series to pillars 30, 31, respectively of Bismuth Tellurium appropriately doped so that an electrical current passing between the pillars 30, 31 by way of the copper base 14 induces the same temperature effect, in this case cooling, at the two junctions 12 and 13. The pillars 30, 31, are embedded in a polyester resin known commercially as DISCON polyester embedded resin available from Synthetic Resins Pty., Ltd., and used with MEKP Catalyst, and their ends are thermally, mechanically and electrically united with respective blocks of high conductivity copper 32, 33, providing heat sinks and which are of parallelepiped shape. Grooves 34 are provided in the copper to provide keying for the resin.

A pair of horns 40, 41 extend upwardly from the blocks 32, 33 and are arched over at their upper ends to provide arms 43, 44. These horns are made of copper and the arm 43 has mounted within it a light emitting diode (LED) 45 positioned to direct a beam of red light onto the exposed area 18 of the mirror surface of the member 11. The LED diode 45 is available from Hewlitt Packard and is type No. 5082-4658. The second arm 44 carries a light-sensitive resistor 49 cast in a transparent block to withstand temperature of the order of 65° C for a short time. The resistor 49 is a Phillips Elcoma type 2322-600-94001. A mask 50 ensures that a single cell only of the resistor is exposed. The resistor 49 comprises two spaced interdigitated combs having straight, parallel spaced teeth and a "single cell" is to be understood as meaning an area of the resistor containing only two parallel sections of two neighbouring teeth of respective combs and the space between them. A characteristic of this cell is that its electrical resistance exhibits a relatively sharp kink when the light incident on it falls beneath a threashold value. The light path between the LED 45 and the cell of the resistor makes an angle of 45° with the plane of the area 18 and the red silicone rubber coating 47 which defines the area 28 provides a sharp edge which cuts off light travelling to and from the mirror area 1 making an angle, through refraction, of less than 45°. As the silicone rubber coating is red, it absorbs the red light emitted by the LED which has a pre-focussed lens system.

The LED is connected on one side to the arm 43 so that it shares the current input terminal 80 of the Peltier junctions whose current output terminal 81 is shared with one side of the light-sensitive resistor 49. In this way the number of leads are reduced. The electrical circuit to the wire 22 of the thermistor is completed by way of a wire 60 which is welded at 50 to the copper base 14 of the member 11 on its side which is on the diametrically opposite side of the area 18 to the joint 23. The thermister current is held at a low constant value to prevent thermal interference.

Figure 3:
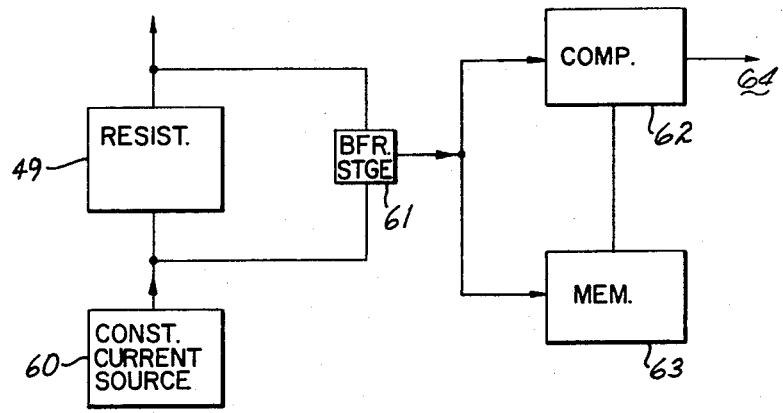
FIG. 3 is an electrical circuit to a light-sensitive detector.

FIG. 3 shows the electrical circuit to the light-sensitive resistor 49. The resistor 49 is fed by a constant current source 60 which may be any one of a large number of electronic circuits well-known in the art for providing a constant current irrespective of the light applied to it. In consequence, changes in the light falling on the resistor produce a change in the voltage across it. This voltage is transmitted via a buffer stage with a high input impedance and low output impedance to a comparator 62 which is fed with a reference voltage from a memory 63. This memory is loaded with the buffer stage output voltage at the beginning of a dewpoint measurement and is therefore independant of parameters of the electrical circuitry which can change over long periods of time. As the duration of measurement is only a few seconds, the value loaded in the memory 63 is indicative of the resistance of the temperature sensitive resistor 49 when receiving reflected light from the LED 45 at the beginning of a measurement.

As soon as the light incident on the resistor 49 traverses the sharp bend in the light cell characteristic, the input to the comparator from the buffer stage 61 changes dramatically and the comparator responds to the difference from the reference value by providing an output on terminal 64 signifying that the dewpoint temperature has been reached.

Figure 4:
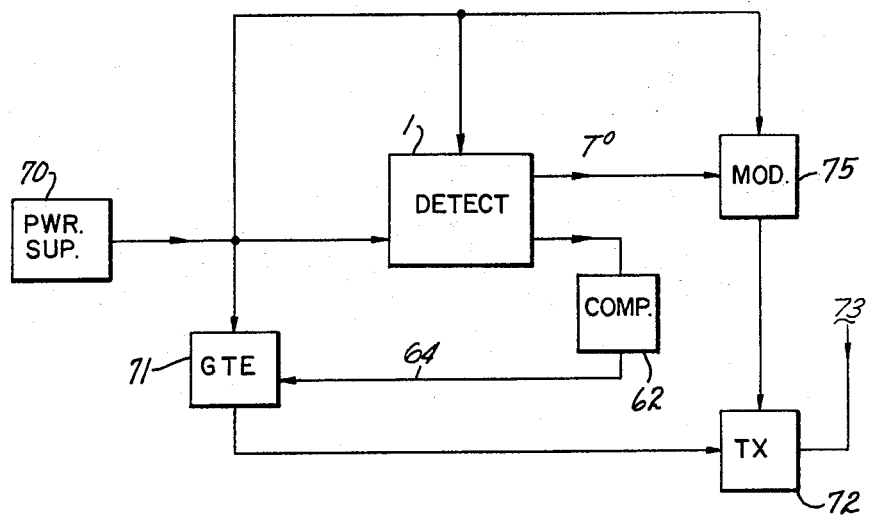
FIG. 4 is a block diagram of one way of using the device.

FIG. 4 shows in block form the remainder of the circuit. It comprises an electrical power supply 70 feeding the dewpoint detector 1 and also a gate 71 which is held closed until a signal appears on lead 64 signifying that the dewpoint temperature has occurred. This opens the gate 71 to allow energisation of a radio transmitter 72 feeding an aerial 73. The thermistor electrical output of the device is fed to a modulator 75 and used to provide mark space modulation of the transmitter, the ratio of mark to space being significant of the temperature sensed by the thermistor.

OPERATION OF PREFERRED EMBODIMENT

The above described apparatus operates as follows; When switched on, for example by a remotely actuated isolating switch, the power supply 70 energises the detector 1 and modulator 75. The LED 45 directs a beam of light at 45° on to the mirror area 18 and the reflected beam is picked up by the light-sensitive cell 49. The thermistor circuit is energised so that the modulator 75 receives the temperature as measured by the thermistor 21. As current is fed through the two junctions 12, 13, heat is extracted from them, and they cool the bridge 11. The exposed area 18 on which the light is incident is thus cooled from both sides and its temperature is continuously monitored by the thermistor 21. When the dewpoint is reached, a layer of condensation forms on the area 18 and the light output to the light sensitive resistor 49 drops sharply. The comparator 62 of FIG. 3 responds and opens the gate 71 so that the power supply can energise the transmitter which, simultaneously, is modulated by the output of the modulator 75. A radio transmission then takes place for a predetermined time and the modulation of the transmitter output is a measure of the dewpoint temperature.

After dewpoint measurement has taken place the power supply is switched off, preferably automatically, and the temperature of the heat sinks 32, 33 is transmitted back through the pillars 30, 31 to the bridging member 11 to raise its temperature initially above the ambient temperature so that the layer of condensate formed on the exposed area 18 is quickly evaporated.

It is important that the nickel surface of the bridging member 11 is cut back and highly polished in order to provide a nickel surface relatively free of indentations.

Preferably the current to the Peltier junctions is pulsed in order to reduce the thermal inertia and thus the formation of a temperature gradient between the junctions 13 and 12 and the area 18, as much as possible. The fall in temperature of the bridging member 11 can then be arranged to occur gradually and the temperature indicated at which condensation occurs on the area 18 is a more precise and accurate measure of that temperature.

Figure 2:
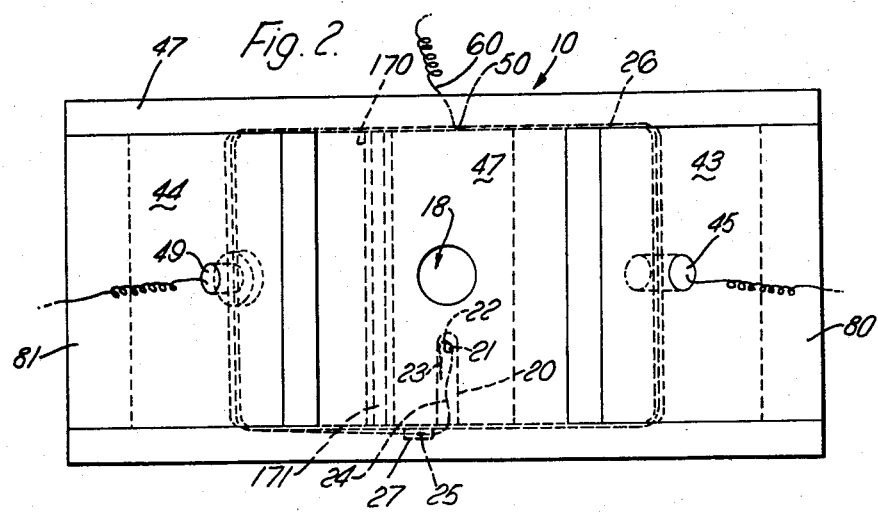
FIG. 2 is a top plan view of the device.

The approximate overall dimensions of the device shown in FIGS. 1 and 2 are 2 inches by 1½ inch by ½ inch and the electronic circuitry can be miniaturised so that the entire system shown in FIG. 4 can be made very small indeed.

It will be appreciated that the above described device can be made and sold separately for use with any form of temperature-sensing equipment and is not necessarily limited to use with the circuitry shown in FIGS. 3 and 4.

As previously stated the invention has numerous applications not related to recording dewpoint temperature. It can, for example, be used in a transparent liquid to signify when freezing of a constituent of the liquid occurs. For example impurities disolved in the liquid can be detected by their freezing temperatures as the formation of ice on the mirror will impair its reflectivity and the temperature at which freezing occurs depends on the nature of the environment as well as other factors. Another use is recording moisture in a fluidized bed. A further use is sensing water in non-acqueous liquids. It is also useful in relation to measuring intravenous solutions water content. A further use is in microcombustion analysis where it enables the extent of water decomposition in a closed cell to be monitored and measured. Yet a further use is in the control field where it is necessary to observe a particular level of humidity for a reaction to take place. The device of the invention can also be used to sample the humidity periodically and to adjust, automatically, control equipment to maintain the humidity within predetermined limits. An example of such a use is described in detail in our Australian copending application filed simultaneously with this application and by the same inventor, the example being concerned with the control of a gas sterilizer.

Various changes can be made to the apparatus described above. For example, to enable it to be used in daylight the light source 45 is preferably of high intensity type providing an intense collimated beam of red light and the light-sensitive resistor 49 is matched and responds preferentially to red light of the wavelength of the source 45. It is important that the light sensitive resistor 49 is masked to expose only a very small area of its surface comprising a single cell to the incident light, say 1.5mm$^2$, and that the incident light from the source just covers the small area exposed. The optical effects produced as soon as clouding of the mirror occurs produces a divergence and shift of the collimated light incident on the exposed small area of the resistor and a consequential fall in sensed light intensity occurs which changes the electrical output of the resistor 49. It is possible to detect, in this way, as little as a 4% attenuation of the nominal reflected light from the mirror with repeatible accuracy and thus a very accurate measurement of the dewpoint temperature is obtained in a way which ensures that the molecular thickness of the moisture deposited on the mirror is insufficient to dissolve in it many gaseous impurities which, in dissolved form, would mar the mirror's reflecting characteristics. Thus, by detecting accurately the onset of misting before any substantial misting has occurred, and by ensuring that the mirror temperature, during measurement, does not fall to a value at which the vapour film is thick enough to dissolve gaseous mirror contaminants, the maintenance of the reflectivity of the mirror is prolonged, the accuracy of the device is maintained, and sampling of the dewpoint can be repeated at relatively very frequent intervals.

It should be pointed out that currently available light-dependent resistors (LDR) are often temperature sensitive so that re-setting of the electronic equipment which responds to the LDR output is necessary at frequent intervals. Such re-setting is conveniently carried out by a sampling hold circuit as described in detail in our said Australian application filed on even date herewith, by the same Inventor, and covering the use of the device to control the humidity within a sterilizer.

MODIFICATION OF PREFERRED EMBODIMENT

In a modification of the device shown in FIG. 1, the insulated constantine wire is not coiled around the groove 15 of the copper base 14 but is, instead, formed as a long wire coil embedded in said Thermaflow putty in a linear channel cut through the top face of the nickel layer 16 and spaced to one side of the exposed surface 18. This channel is shown in dotted outline at 70 in FIGS. 1 and 2. The advantage obtained from this small modification is that the change in length of the periphery of the base 14 with change in its temperature does not stress the constantine wire when arranged in a coil in a linear channel. The temperature of the wire is still, however, that of the base 14.

For certain applications which are critical in that they require better than ½% resolution e.g., the measurement of moisture or a gaseous organic solvent in a fractionating column, the output of the light source provided by the LED 45 must be stabilised. This may be achieved by monitoring a part of the light output not incident on the area 18 and using it to control the electrical supply to the LED in a way which maintains its light output constant. Also, for critical applications, the light sensitive resistor may be a Phillips Elcoma RPY 55.

In addition to measuring the temperature of a dewpoint, the device of the invention may also be used to measure the freezing point as the reflectivity of a mirror changes suddenly if a transparent liquid contacting its surface suddenly freezes.

We claim:

1. A phase-transition, temperature-detecting device comprising a Peltier effect junction; electrical circuitry means operable to drive a current through said junction to produce cooling thereof; a member having good thermal and electrical conducting properties and cooled by said junction, a discrete area on said member providing an exposed mirror; a temperature-sensitive electrical component buried in said member; first and second electrical connections extending from said component; means thermally clamping said electrical connections to said member whereby said member provides a heat sink for said connection, the first connection being mechanically and electrically connected to said member; a lead connected to said member at a remote location from said first connection; and, transition temperature responsive and registering means connected electrically to said lead, whereby the occurrence of a transition temperature is detected by said mirror, the reflective properties of which deteriorate suddenly when clouded by the occurrence of the transition temperature and the temperature at which this transition occurs is registered by the temperature responsive means.

2. A device as set forth in claim 1, in which an extended length of wire provides the second of said electrical connections and said wire is externally insulated from but thermally clamped along its length to said member.

3. A device as set forth in claim 1, including thermal insulating material covering said member apart from said discrete area, a light source arranged to direct light onto said discrete area, and a light detector arranged to receive reflected light from said discrete area, the light path between the source and detector being at substantially 45° to the discrete area and a material defining the area intercepting light which makes an angle of less than substantially 45° with the discrete area.

4. A device as set forth in claim 3, in which said material is red and the light source is a LED emitting red light.

5. A device as set forth in claim 3 in which said light detector comprises a light sensitive resistor, a plurality of light cells formed on the surface of said resistor, and means masking the resistor surface apart from 1 to 2 of said cells whereby the electrical characteristic curve of said resistor has a sharp bend.

6. A device as set forth in claim 3, in which said light detector comprises a light sensitive resistor, a constant current electrical source is serially connected to said resistor, and a comparator is connected thereto to compare a reference voltage with a voltage which is a function of that across the resistor, to determine the moment at which the phase transition occurs.

7. A device as set forth in claim 3, in which said light detector comprises a light sensitive resistor, a comparator connected thereto to compare a reference voltage with a voltage which is a function of that across the resistor, including voltage storage circuit means, means providing said reference voltage from an electrical value stored in said storage circuit means, and further means acting to update the value stored in said storage circuit means so that it is a measure of the electrical output of the detector immediately prior to the next operation of the device.

8. A device as set forth in claim 1, in which parts of the device provide said heat sink, horns are provided on said parts, and said light source and said detector are provided on respective horns.

9. A device as described in claim 1, in which said discrete area of said member providing a mirror is mounted between two Peltier junctions both on the same side of the member and formed by the ends of electrically conductive pillars which are each provided with its own heat sink block of electrically conductive copper from which horns extend, said junctions being p-doped and n-doped respectively.

10. A device as described in claim 11, in which said temperature sensitive electrical component is located spaced to one side of the discrete area and on substantially the same isotherm in the member.

11. A device as claimed in claim 4, in which the extended length of wire is arranged as a coil embedded in putty in a channel in the member.

12. A device as claimed in claim 4, in which an extended length of wire in a channel of the member provides the second of said electrical connections, the channel extending linearly between one pair of opposite sides of the member and lying between said discrete area and one of the member-cooling junctions so as to be relatively unafffected by thermal changes in shape of the member during operation of the device.

13. A device as claimed in claim 12, in which the channel is cut in the same surface of the member as that in which the discrete area is formed.

* * * * *